United States Patent [19]

Schweighardt et al.

[11] Patent Number: 4,895,876
[45] Date of Patent: Jan. 23, 1990

[54] CONCENTRATED STABLE FLUOROCHEMICAL AQUEOUS EMULSIONS CONTAINING TRIGLYCERIDES

[75] Inventors: Frank K. Schweighardt, Allentown; Charles R. Kayhart, Alburtis, both of Pa.

[73] Assignee: Air Products and Chemicals, Inc., Allentown, Pa.

[21] Appl. No.: 28,521

[22] Filed: Mar. 20, 1987

[51] Int. Cl.$^4$ .................. A61K 31/35; A61K 31/334; A61K 31/445; A61K 31/535

[52] U.S. Cl. ................................ 514/747; 514/231.2; 514/315; 514/451; 514/461; 514/723; 514/749; 514/743; 514/751; 514/755; 514/756; 514/757; 514/758; 514/759; 514/760; 514/761

[58] Field of Search ............... 514/759, 743, 755, 756, 514/749, 758, 766, 761, 747, 231.2, 315, 451, 461, 723, 751, 755

[56] References Cited

U.S. PATENT DOCUMENTS

| | | | |
|---|---|---|---|
| 3,962,439 | 6/1976 | Yokoyama et al. | 424/248 |
| 4,397,870 | 8/1983 | Sloviter | 424/325 |
| 4,423,077 | 12/1983 | Sloviter | 424/325 |
| 4,443,480 | 4/1984 | Clark, Jr. | 424/352 |
| 4,497,829 | 2/1985 | Sloviter | 514/672 |
| 4,533,254 | 8/1985 | Cook et al. | 366/176 |
| 4,866,096 | 9/1989 | Schweighardt | 514/756 |

FOREIGN PATENT DOCUMENTS

| | | | |
|---|---|---|---|
| 0220153 | 4/1987 | European Pat. Off. | 514/759 |
| 2091098 | 7/1982 | United Kingdom | 514/759 |

OTHER PUBLICATIONS

L. C. Clark, Jr., "Pathophysiology of Shock, Anoxia, and Aschemia", p. 507, Williams and Wilkins Publishers (1982).

Dr. Robert Geyer, "Synthesis and Biological Screening of New and Improved Fluorocarbon Compounds for Use as Artificial Blood Substitues", Harvard University School of Public Health (RFP-NHLI-HB-75-19).

Edward M. Levine et al, "Artificial Blood" on the Laboratory Horizon (LAB World).

Jean G. Riess, "Reassessment of Criteria for the Selection of Perfluorochemicals for Second Generation Blood Substitutes. Analysis of Struture/Property Relationships", published in Artificial Organs, 8(1):44–56, Raven Press, New York 1984.

Industrial and Engineering Chemistry, vol. 39, p. 380 (1949), Journal of Chemical Society, 1950, p. 3617 and Advance of Fluorine Chemistry, vol. I, p. 129 (1960).

*Primary Examiner*—Floyd D. Higel
*Attorney, Agent, or Firm*—Geoffrey L. Chase; James C. Simmons; William F. Marsh

[57] ABSTRACT

A stable concentrated aqueous emulsion of perfluorochemical, a phospholipid and a triglyceride of fatty acids has been demonstrated which has enhanced stability, diminished particle size and heightened tolerance by biological systems. The emulsion has utility as an oxygen transport medium, such as artificial blood. The emulsion can optionally include additional emulsifiers of SURFYNOL®SE surfactant and PLURONIC® P-105 surfactant. The emulsion is produced using an improved emulsification technique. The invention includes methods of oxygen transport in vascular systems wherein the oxygen carrying capacity of the vascular systems is improved with the emulsions of the present invention. Methods are also described for organ preservation extra-vivo by perfusing, suffusing, flushing and filling organs outside the body with the oxygen carrying emulsions of the present invention. Finally, methods of synthesis of the emulsions by emulsifying the components and aqueous medium using high shear mixing is also described.

20 Claims, No Drawings

CONCENTRATED STABLE FLUOROCHEMICAL AQUEOUS EMULSIONS CONTAINING TRIGLYCERIDES

TECHNICAL FIELD

The present invention is directed to biologically acceptable oxygen transport media comprising high concentration aqueous emulsions of perfluorochemicals in complex emulsification systems. More specifically, the present invention is directed to an aqueous perfluorochemical emulsion having utility in the field of resuscitative fluids for oxygen transport and volume expansion in mammals, such as artificial or synthetic blood.

BACKGROUND OF THE PRIOR ART

It is generally known that some kinds of fluorocarbon emulsions have utility as resuscitative fluids or blood substitutes, wherein the fluorocarbon acts as an oxygen transport medium in place of the hemoglobin function in natural blood of mammals.

Fluorocarbon particle size has been identified as a factor in toxicity and has adverse effects upon biological systems, such as test animals wherein particles having a size of 0.4 micron or average particle size of greater than 0.2 micron have been identified as problematic to effective maintenance of such test animals.

In light of the requirement for extremely small fluorocarbon particle size in stable emulsions for blood substitute or oxygen transport utility, difficulties in appropriate emulsification and stability under general storage conditions exist due to the incompatibility of the fluorocarbons and their aqueous medium in which they are emulsified. Further, it has generally been found that surfactants pose a problem of biocompatibility.

Various fluorocarbons have been utilized for experimentation in the area of oxygen transport in mammals, including perfluorotripropylamine. perfluorodecalin, perfluoromethyldecalin and perfluorotributylamine.

Various emulsifiers have been utilized to emulsify fluorocarbons in an aqueous phase, including the PLURONIC ® surfactants having a chemical structure of polyoxyethylene-polyoxypropylene copolymer, lipids, most notably lecithin from egg yolk phospholipids and soybean phospholipids and the monoglyceride of fatty acid selected from the group consisting of caprylic acid, capric acid, lauric acid, myristic acid, palmitic acid, stearic acid, behenic acid, palmitoleic acid, oleic acid, linolenic acid and arachidonic acid.

These fluorocarbons and emulsifiers are dispersed in aqueous media having physiological acceptance, including isotonic solutions such as Tyrode solution, Ringer's solution, lactated Ringer's solution or Ringer's solution containing glucose, and in some instances such aqueous media include emulsifier adjuvants, such as traces of fatty acid.

In U.S. Pat. No. 3,962,439, an artificial blood is set forth having a perfluorocarbon of 9–11 carbon atoms, a particle size of 0.05–0.3 microns and an emulsifier of a phospholipid and an emulsifying adjuvant of a fatty acid, its salt or the monoglyceride of such fatty acid. The fluorocarbon comprises a 10–40% weight to volume concentration in an emulsion containing 2–6% weight/volume of a phospholipid and minor amounts of fatty acid.

In U.S. Pat. No. 4,397,870 a process is set forth for the prolonged stability of perfluoro compounds in animals and humans comprising injecting an emulsifying agent into the perfused individual. The patent recites that the perfluoro compound represents 15–40% volume per volume of the total mixture which corresponds to 30–75 percent weight per volume and 7–9% weight per volume of lecithin.

U.S. Pat. No. 4,423,077 describes a stable emulsion of perfluoro compounds having a content of 30–75% weight per volume and a 7–9% weight per volume of a lipid which coats the perfluoro compound in a physiologically acceptable aqueous medium. The emulsion of this patent has a particle size of approximately 0.1 micron and 95% of the particles had diameters below 0.2 microns.

U.S. Pat. No. 4,497,829 is directed to stable emulsions prepared by dispersing a purified lipid in a physiologically acceptable aqueous medium by sonication, adding perfluoro compound to the dispersion, sonicating the mixture of lipid in perfluoro compound to form an emulsion of lipid-coated particles of perfluoro compound and centrifuging the emulsion formed to separate oversized particles.

The present inventors are aware of work that produced low levels of perfluorochemicals (0–50 wt/vol %) in LIPOSYN ®II nutrient emulsion, available from Abbott Laboratories. North Chicago, Ill. That work was not capable of producing higher perfluorochemical concentrations.

The present invention provides an advance over the prior art of artificial blood media to provide high fluorochemical concentrations, decreased particle size, increased stability without freezing and longer shelf life for an oxygen transport media useful in mammals. The high level concentrations of fluorochemical are particularly important due to the necessity to carry sufficient oxygen to living tissues.

BRIEF SUMMARY OF THE INVENTION

The present invention represents a stable aqueous emulsion of a perfluorochemical comprising approximately 60 weight/volume percent or greater of a perfluorochemical, approximately 0.5 up to 7 weight percent of a phospholipid which emulsifies said perfluorochemical and approximately 5–30 weight percent of a triglyceride of fatty acids with the remainder comprising an aqueous medium.

Preferably, the perfluorochemical is selected from the group consisting of perfluoroalkylcyclohexane having 3–5 carbon atoms in the alkyl group, perfluorooctylbromide, perfluorodecalin or perfluoromethyldecalin. Optimally, the perfluorochemical is perfluorodecalin.

Preferably, the emulsion contains approximately 75 weight/volume percent of the perfluorochemical. Preferably, the phospholipid is present in the range of 1–2 wt %. Preferably, the triglyceride of fatty acids is present in the range of approximately 5–30 wt %, preferably 10–20 wt % and optimally approximately 20 wt %.

Preferably, the phospholipid is an egg phosphatide. Preferably, the triglyceride of fatty acids is selected from the group consisting of safflower oil, soybean oil or mixtures thereof.

Alternatively, the emulsion contains an additional emulsifier adjuvant comprising an acetylenic diol, such as SURFYNOL ®SE and/ or a polyoxyethylene polyoxypropylene copolymer such as PLURONIC ®P-105.

Optimally, the present invention consists of a stable emulsion in a physiologically acceptable aqueous medium of an oxygen-transferable saturated perfluorodecalin having essentially no detectable hydrogen or olefinic character and a mean particle size of about 0.15 microns which comprises said perfluorodecalin in a concentration of 60–90 weight/volume percent, a phospholipid as an emulsifier in a concentration of approximately 1.2 wt %, at least one triglyceride of fatty acids as an emulsifier adjuvant in a concentration of 10–20 wt % wherein the fatty acids have 16–18 carbon atoms, and glycerin in an amount of approximately 2.5 wt %, said emulsion being suitable for use as a blood substitute.

Preferably, the above emulsion includes an additional emulsifier adjuvant of an acetylenic diol and/or a polyoxyethylene polyoxypropylene copolymer.

It is also possible for the emulsion to contain other non-toxic adjuvants to render the emulsion isotonic, to provide various electrolytes, nutrients or antibiotic effect as long as the adjuvants do not interfere with stability, particle size or oxygen transport.

DETAILED DESCRIPTION OF THE INVENTION

In the present invention, various perfluorochemicals are known to be useful as oxygen transport components of mixtures for various biological systems. These perfluorochemicals are typically perfluorocarbons which can include three groups but are not limited to these groups.

The first group of the perfluorocarbon compounds used in the invention is a perfluorocycloalkane or perfluoro(alkylcycloalkane) which includes, for example, perfluoro($C_{3-5}$-alkylcyclohexanes) such as perfluoro(methylpropylcyclohexanes), perfluoro(butylcyclohexanes), perfluoro(trimethylcyclohexanes), perfluoro(ethylpropylcyclohexanes) and perfluoro(pentylcyclohexanes); perfluorodecalin. perfluoro(methyldecalines) and perfluoro(dimethyldecalin) and perfluoroperhydrophenanthrene.

The second group is a perfluoro(alkylsaturated-heterocyclic compound) which includes, for example, perfluoro(alkyltetrahydropyrans) such as perfluoro(butyltetrahydropyrans), perfluoro(pentyltetrahydropyrans) and perfluoro(hexyltetrahydropyrans); perfluoro(alkyltetrahydrofurans) such as perfluoro(pentyltetrahydrofurans), perfluoro(hexyltetrahydrofurans) and perfluoro(heptyltetrahydrofurans); perfluoro(N-alkylpiperidines) such as perfluoro(N-pentylpiperidines), perfluoro(N-hexylpiperidines) and perfluoro(N-butylpiperidine); and perfluoro(N-alkylmorpholines) such as perfluoro(N-pentylmorpholines), perfluoro(N-hexylmorpholines) and perfluoro(N-heptylmorpholines).

The third group is a perfluoro(tert-amine) which includes, for example, perfluorotripropylamine, perfluorotributylamine, perfluoro(diethylhexylamine), perfluoro(dipropylbutylamine) and perfluoro(diethylcyclohexylamine), and a perfluoro(dioxalkane), that is, perfluoro(alkylene glycol dialkyl ether), such as perfluoro(3,8-dioxa-2,9-dimethyldecane) or perfluoro(tetramethylene glycol diisopropyl ether), perfluoro(3,7-dioxa-2,8-dimethylnonane) or perfluoro(trimethylene glycol diisopropyl ether) and perfluoro(4,6-dioxa-5,5-dimethylnonane) or perfluoro(isopropylene glycol di-n-propyl ether).

Additionally, compounds similar to perfluorooctylbromide and other perfluorochemicals are useful.

These perfluorochemical compounds are used alone or in a mixture of their isomers, and further of two or more kinds of the compounds. The compounds may be available on market. Alternatively, they may be produced according to the processes described, for example. in the articles of Industrial and Engineering Chemistry, Vol. 39, page 380 (1949), Journal Chemical Society, 1950, page 3617, and Advance of Fluorine Chemistry, Vol. I, page 129 (1960) or by other fluorination techniques.

The root chemical compound may be essentially completely perfluorinated to remove all hydrogens and unsaturation by a multiple stage fluorination technique. The chemical compound is first subjected to fluorination using a $CoF_3$ particulate bed operated at a temperature of approximately 275°–427° C. The chemical composition is carried through the bed with a nitrogen carrier gas at a pressure of ambient up to 2 psig. The nitrogen to organic ratio is in the range of 10/90 to 90/10. Yields from this fluorination are typically 50 to 80% of theoretical. Alternatively, compounds from the third group above are fluorinated in a Simon cell by well known technology.

The crude fluorochemical obtained from the cobalt trifluoride reactor can be reacted with elemental fluorine to remove trace amounts of residual hydrogen and unsaturation. Preferably the crude fluorochemical is subjected to a fluorine/nitrogen mixture containing 5–100% fluorine. The concentration and flow rate of the fluorine mixture is controlled to maintain temperatures below the boiling point of the fluorochemical. Depending upon the extent of fluorination in the cobalt trifluoride reactors, the direct fluorination is continued for a period of up to 36 hours or until analysis indicates no detectable residual hydrogen or olefinic character.

As an alternative to direct fluorination, multiple passes through the cobalt trifluoride reactor have also been used to minimize residual hydrogen and olefinic character. This is the most commonly reported method.

In addition to the above techniques which convert residual contaminents to the desired product, other chemical extraction techniques have been used for the removal of trace contaminants to produce biocompatible fluorochemicals. A purification method whereby the fluorochemical is reacted with an aqueous alkaline solution in the presence of a secondary amine, has been used to remove residual hydrogen. See L. C. Clark, Jr. *Pathophysiology of Shock, Anoxia, and Aschemia*, page 507, Williams and Wilkins Publishers (1982).

Another method is to sequentially distill the fluorochemical from a slurry containing sodium fluoride, sodium hydroxide and potassium permanganate. See Dr. Robert Geyer, *Synthesis and Biological Screening of New and Improved Fluorocarbon Compounds for Use as Artificial Blood Substitutes*, Harvard University School of Public Health (RFP-NHLI-HB-75-19).

The perfluorochemical is then subjected to distillation and filtration through successive beds of sodium fluoride, activated carbon and alumina to result in the ultrapure perfluoro compounds preferred for biological applications of the subject emulsion compositions.

Among the perfluorochemical compounds mentioned above, the most preferable ones are perfluorodecalin, perfluoro(methyldecalin) and perfluorooctylbromide owing to their more rapid excretion from the body, their known biocompatibility and their availability. The fluorocarbon is present in the emulsions of the present invention in the range of approximately 60 wt/vol percent or greater, but generally in the 60–90 wt/vol % range. The term wt/vol % as used throughout this text is based on grams of perfluorochemical divided by the total milliliters of emulsion.

The phospholipid emulsifier is generally a naturally occurring and recovered lipid from egg yolk or soybean derivation. These phospholipids preferably comprise yolk lecithin or soybean lecithin, generally known as monoaminomonophosphatide compounds. The egg phosphatides are preferable.

Egg phosphatides, purified, are primarily a mixture of naturally occurring phospholipids which are isolated from egg yolk. These phospholipids have the following general structure:

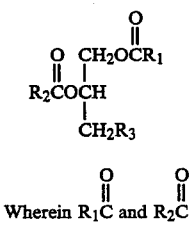

are the same saturated and unsaturated fatty residues that abound in neutral fats. $R_3$ is primarily either the choline [$HOCH_2CH_2N(CH_3)_3OH$] ester or ethanolamine ($HOCH_2CH_2NH_2$) ester of phosphoric acid ($H_3PO_4$).

The emulsifier adjuvant generally comprises a neutral triglyceride of various long chain fatty acids ($C_{16}$–$C_{18}$) including linolenic, oleic, palmitic, stearic and linolenic acids. Such neutral triglycerides are generally available from a wide range of natural sources, including safflower oil and soybean oil. When the emulsifying adjuvant of the present invention comprises a 50/50 mixture of safflower oil and soybean oil, then the fatty acid components comprise approximately 65.8% linolenic acid, 17.7% oleic acid, 8.8% palmitic acid, 3.4% stearic acid and 4.2% linolenic acid. Although the triglyceride level can be as low as approximately 5–10 wt %, it is preferable to use a triglyceride level of approximately 20 wt % based upon the aqueous emulsion prior to admixture with the perfluorochemical.

The triglyceride-containing aqueous emulsifier used in the examples set forth below comprises Abbott Laboratories LIPOSYN® II (10% and 20%) emulsion which contains 5–10% safflower oil, 5–10% soybean oil, 1.2% egg phosphatides and 2.5% glycerin in water. Sodium hydroxide is added to adjust the pH to 8–8.3. LIPOSYN® II emulsion is available from Abbott Laboratories, North Chicago, Ill. 60064.

The emulsion according to the present invention is preferably isotonic, containing an appropriate amount of sodium chloride or other electrolytes, including components in Ringer's solution or lactated Ringer's solution. Additionally, glycerine is present in an amount of approximately 2.5%.

The emulsion of perfluorochemical compound according to the present invention contains some particles of the perfluorochemical having a size less than 0.1 microns and a mean particle size of about 0.15 microns. These perfluorochemical particles are in stable emulsion in an autoclaved sterile aqueous system for periods of time exceeding 8 weeks at room temperature.

To enhance the reduced particle size of the emulsions and provide additional assurance of stability, additional emulsifier adjuvants may be added. For instance, the emulsions of the present invention have been enhanced in smaller particle size and increased stability by the addition of a combination of SURFYNOL®SE surfactant which is an acetylenic diol available from Air Products and Chemicals, Inc. and PLURONIC® P-105 surfactant which is a polyoxyethylene-polyoxypropylene copolymer which is available from Wyandotte Chemical Corporation, Wyandotte, Mich. These additional emulsifier adjuvants may be added in concentrations of up to 2.0 wt %.

Albumin, such as bovine serum albumin can be added to the present emulsions in an amount of 0.2 to 2.0 weight percent, preferably 1.0 weight percent to act as an oncontic agent for better control of emulsion particle and to avoid adverse effects of the emulsion on muscle cells of the heart of a mammal which is administered the emulsion.

Previous emulsions of perfluorochemical and LIPOSYN®II emulsions were possible in the concentration ranges of 10–50 wt/vol % perfluorochemical. However, using conventional preparation techniques, the upper limit of perfluorochemical concentrations was 50 wt/vol % perfluorochemical. Above these concentrations, conventional processing denatured the constituents of the emulsion and achieved coagulation of components in the remaining liquid phase.

The present invention provides an unexpected high concentration perfluorochemical emulsion of approximately 60–90 wt/vol % or higher without component denaturing or coagulation. This concentration range is achieved by special processing techniques, including the incremental addition of perfluorochemical to the aqueous phase emulsion and maintenance of relatively cool temperatures of the emulsion during the microfluidization emulsification process. Perfluorochemical is added to the emulsification process preferably at temperatures as low as 4° C., but during severe mixing conditions temperatures rise even under significant cooling so that maintenance of temperatures in the range of 20°–35° C. is considered acceptable.

To achieve the high concentration emulsions of the present invention, it has been found necessary to subject the perfluorochemical and its emulsifier to high shear mixing wherein the simple admixture of the components are split and impinged upon one another at liquid velocities of 132–1650 ft/sec. to achieve a high energy impact of the components. Pressures of 13,000 to 15,000 psig have been found to facilitate appropriate mixing and emulsification. Appropriate mixing can be achieved in a Microfluidic's Model 110 Microfluidizer apparatus, as per U.S. Pat. No. 4,533,254 incorporated herein by reference.

The concentration ranges for the subject perfluorochemical emulsions of the present invention are set forth below:

| | |
|---|---|
| (A) | Perfluorochemical: approximately 60 wt/vol percent or greater; |
| (B) (i) | LIPOSYN ® II 10% emulsion: 50–95 volume percent or |
| (ii) | LIPOSYN ® II 20% emulsion: 30–95 volume percent, and optionally; |
| (C) | SURFYNOL ® SE surfactant: 0.0–0.6 wt percent; |
| (D) | PLURONIC ® P-105 surfactant: 0.0–2.0 wt percent; |
| (E) | Water: 0.0–40 volume percent (additional water beyond that present in the LIPOSYN ® II emulsions); and |
| (F) | Electrolytes: as necessary to make the emulsion isotonic. |

The perfluorochemical emulsion is prepared according to the following procedure and examples setting forth the emulsification of the above-identified components.

PRESENT INVENTION EMULSIFICATION TECHNIQUE

The process used to create the emulsions of the present invention consists of the following steps:

1. The Microfluidizer mixing apparatus is alcohol (ethanol) sterilized by passing 250 ml of a 75 vol % alcohol/water solution through the system for 10 minutes at 10,000 psi back pressure. All components that are removable were steam sterilized at 120° C. for 15 minutes in an autoclave. All water, perfluorochemical and associated glassware are steam sterilized. LIPOSYN ® II emulsion was used "as received" from Abbott Labs as a sterile injectable nutrient fat emulsion.

2. LIPOSYN ® II emulsion is added into the feed reservoir at 4° C. and circulated for five minutes as the pressure is increased from 0 to 14,500 psi. When the pressure remains constant for 30 seconds, one-half of the perfluorochemical volume is added at a rate of 4-5 ml/minute. The resulting partial emulsion is removed from the unit and cooled to 4° C. Processing of the emulsion causes an increase in temperature of 20°-30° C. The temperature must be controlled to cause a stable system to result at high perfluorochemical loadings (>40 wt/vol %) and to avoid denaturing of the emulsifier. At all times the reaction zone, transfer lines and filters are kept at 4° C. with ice/water slush. After the partial emulsion is cooled to 4° C., processing is continued. The remaining 50 volume percent of the perfluorochemical is added at a rate of 6-8 ml/minute with the back pressure at 14,500 psi. When the last volume of perfluorochemical is added, the total emulsion is processed for an additional five minutes. At the stated conditions, the nominal 100 ml volume is processed eight times per minute for a total of 70-80 passes through the Microfluidizer apparatus reaction zone. At all times the fluid being processed is kept below 35° C., preferably below 20° C.

EXAMPLE I (8469-104-1)

Perfluorodecal in (82 grams) was combined with LIPOSYN ® II/20% emulsion (75 grams) at 4° C. in a Microfluidic's Model 110 Microfluidizer apparatus to prepare a 70 wt/vol % perfluorodecalin emulsion using the above methodology.

The resulting emulsion is a light, milky white fluid with a mean particle size of 0.15 microns as measured by laser light scattering. Oxygen solubility as measured by the CAVITRON/LEXO$_2$CON-K ™ Model OC-60 analyzer, manufactured by Lexington Instruments Corp. of Waltham. Mass., is 16 ml oxygen per 100 ml of emulsion at 25° C. and atmospheric pressure. The pH of the non-buffered system was measured to be 6.71 with a free fluoride concentration of <0.2 ppm as determined by specific ion electrode. The surface tension was measured to be 34 dynes/cm at 25° C. The final fluorochemical concentration is 70 wt/vol % perfluorodecalin. The sample has remained stable (no phase separation, i.e. less than 10% increase in mean particle size distribution) at both 4° and 25° C. for 30 days. The emulsion was steam sterilized and did not experience creaming (phase separation).

EXAMPLE II (8469-104-2)

An emulsion of perfluorodecalin (82 grams) LIPOSYN ® II/20% emulsion (75 grams), 0.392 grams SURFYNOL ® SE surfactant and 0.78 grams PLURONIC ® P-105 surfactant was prepared using the process described in Example I to arrive at an approximately 70 wt/vol % perfluorodecalin emulsion.

The addition of SURFYNOL ® SE surfactant and PLURONIC ® P-105 surfactant contribute to the reduction in mean particle size to 0.1 microns. It was observed that the stability of the emulsion increased such that over 30 days at 25° C. there was no measurable increase in mean particle size. The pH in the unbuffered emulsion was 7.2. Oxygen solubility was 16 ml/100 ml at 25° C.

EXAMPLE III (8469-58-3)

Perfluoroperhydrophenanthrene (48 grams) was combined with 72 grams of LIPOSYN ® II 10% emulsion at 4° C. in the Microfluidizer apparatus. The process was as described below under the Prior Art Emulsification Technique.

The resulting emulsion had a particle size distribution of 0.09-0.15 microns. Oxygen solubility was 11 ml/100 ml of emulsion. The pH was 5.8 and the free fluoride concentration was <0.2 ppm. The surface tension was 37 dynes/cm. Perfluoroperhydrophenanthrene was 50 wt/vol % at 25° C. in this example. This emulsion remained stable for more than 90 days at 4° C.

Emulsions prepared in accordance with the above-described examples have been tested for stability and shelf life as set forth above with good results.

EXAMPLE IV (9395-9-1)

Perfluorodecalin (110 grams) was combined with 67 grams of LIPOSYN ®II 20% emulsion to make a 90 wt/vol % emulsion. The following procedure was utilized.

A Microfluidizer ® apparatus was loaded with 67 grams of LIPOSYN ® 11 (20% emulsion). The system was started up in recycle mode at about 5000 psi. The base pan was filled with ice and cooling liquid circulating through the heat exchange coil in cooling vessel. Half of the perfluorodecalin was slowly added to the system, and at the same time a dry ice and methanol slurry was slowly added to the cooling vessel while increasing the pressure to 15,000 psi. The system operated for five minutes. The remaining perfluorodecalin was slowly added to the system and then the system was kept running for an additional five minutes. During the running time, additional dry ice is added to the cooling vessel to maintain cooling of the emulsion during processing. After a total run time of ten minutes, the sample was withdrawn from the system and was in a stable emulsion condition. The temperature of the emulsion when withdrawn was 32° C. The emulsion was placed under refrigeration and after 14 hours, was still in a stable condition.

EXAMPLE V (9395-19-1)

A 70 wt/vol % perfluorodecalin in LIPOSYN II (10%) emulsion was prepared by the emulsification technique of the present invention set forth above with the following specific characteristics.

| 90.00 grams perfluorodecalin | 45 ml | Initial temperature | = 18° C. |
|---|---|---|---|
| 83.00 grams LIPSOYN II (10%) | 83 ml 128 ml | Process temperature Withdrawal temperature | = 20–30° C. = 20° C. |
| 90/128 × 100 = 70.3 wt/vol % | | | |

A stable emulsion formed and was stable after 19 days.

EXAMPLE VI (9395-19-2)

An 80 wt/vol % perfluorodecalin in LIPOSYN II (10%) emulsion was prepared as above, but with the following characteristics.

| 90.00 grams perfluorodecalin | 45 ml | Initial temperature | = 20° C. |
|---|---|---|---|
| 67.00 grams LIPSOYN II (10%) | 67 ml 112 ml | Process temperature Withdrawal temperature | = 20–30° C. = 20° C. |
| 90/112 × 100 = 80.4 wt/vol % | | | |

A stable emulsion formed and was stable after 19 days.

EXAMPLE VII (9393-19-3)

A 90 wt/vol % perfluorodecalin in LIPOSYN II (10%) emulsion was prepared as above, but with the following characteristics.

| 110.00 grams perfluorodecalin | 55 ml | Initial temperature | = 17° C. |
|---|---|---|---|
| 67.00 grams LIPSOYN II (10%) | 67 ml 112 ml | Process temperature Withdrawal temperature | = 20–30° C. = 23° C. |
| 110/122 × 100 = 90.2 wt/vol % | | | |

A stable emulsion formed and was stable after 19 days.

EXAMPLE VIII (8469-411)

Eighty grams of perfluorodecalin was combined with 320 grams of LIPOSYN ® II/10% emulsion at 4° C. in the Microfluidizer apparatus to arrive at an approximately 20 wt/vol % emulsion. The emulsion was made by the procedure of the Prior Art Emulsification Technique described below.

The resulting emulsion had a pH of 7.3, surface tension of 57 dynes/cm, less than 0.2 ppm free fluoride and contained 6 ml oxygen per 100 ml of emulsion.

This emulsion was used to sustain an isolated rabbit heart by 100% blood exchange using 95% $O_2$ and 5% $CO_2$. The emulsion was diluted 1:1 with Krebs salts. The heart continued to function 40 minutes without exhibiting undue work output.

Without the techniques that are unique to the present inventors, (the incremental perfluorochemical addition and emulsification and of the extreme cooling during emulsification below 35° C., preferably 20° C.), the high concentration emulsions (60–90 wt/vol % or greater of perfluorochemical in an aqueous phase) of the present invention cannot be made. This is demonstrated by the following examples using the previously known emulsification technique.

PRIOR ART EMULSIFICATION TECHNIQUE

LIPOSYN II (10 wt %) nutrient emulsion as supplied by Abbott Labs and perfluorodecalin are combined together into the feed tube of a Microfluidizer. The reaction zone of the Microfluidizer sits on a base and resides within a tray. The tray is filled with crushed ice (0°–4° C.) to cool the reaction zone during microfluidization. The need for cooling is taught as necessary because the process develops heat at the instant of processing. Such cooling reduces vapor loss of perfluorodecalin, vapor pressure >14 torr at 25° C. An additional heat exchanger is installed to the "outlet" line of the Microfluidizer to reduce the temperature of the partially prepared emulsion and allow continuous recycle. Crushed ice is recommended and used to affect cooling the flowing stream. Once the cooling configuration is in place, the master air pump is started and pressure is built-up to read between 13,000 and 15,000 psi on the supplied pressure gauge. Liquids are recycled through the unit for five (5) minutes. Such cycling represents 40–45 complete passes through the reaction zone. After the sample is processed it is collected and cooled to 20° C. prior to storage (4° C.) or analysis.

EXAMPLE IX (9395-13-1)

Fifty (60) grams of perfluorodecalin and 90 ml of LIPOSYN 11 (10%) were combined and processed as described above. After 24 hours 0.5–0.75 grams of perfluorodecalin were observed not to be emulsified. This emulsion is considered to be unstable at 50 wt/vol % PF-decalin.

EXAMPLE X (9395-18-2)

Sixty (72) grams of perfluorodecalin and 84 ml of LIPOSYN II (10%) were combined and processed as described above. After 24 hours 1–2 grams of perfluorodecalin remained at the bottom of the sample. After 72 hours 5–9 grams of perfluorodecalin were observed at the bottom of the sample. This sample underwent "creaming" or separation of the oil from the bulk water phase. A 60 wt/vol % emulsion of a perfluorochemical in an aqueous phase resulted, which was unstable.

EXAMPLE XI (9395-21-2)

A 60 wt/vol % perfluorodecalin in LIPOSYN II (20%) emulsion using the above method was prepared with the following characteristics.

| 72.00 grams perfluorodecalin | 36 ml | Initial temperature Max. process temperature | = 18° C. = 84° C. |
|---|---|---|---|
| 84.00 grams Abbott LIPSOYN (20%) | 84 ml | Withdrawal temperature | = 52° C. |

After five minutes process time, an emulsion was formed. After fifteen hours, about ½ gram of PF-decalin had fallen out of suspension. This emulsion was therefore deemed to be unstable.

EXAMPLE XII (9395-21-1)

A 70 wt/vol % perfluorodecalin in LIPOSYN II (20%) emulsion using the above method was prepared with the following specific characteristics.

| 90.00 grams perfluorodecalin | 45 ml | Initial temperature | = 18° C. |
|---|---|---|---|
| | | Max. process temperature | = 75° C. |
| 83.00 grams Abbott LIPOSYN (20%) | 83 ml | Withdrawal temperature | = 48° C. |

No emulsion formed after five minutes. After an additional five minutes an emulsion still did not form.

A comparison of Examples I–VIII and Examples IX–XII demonstrate that the 60–90 wt/vol % or greater perfluorochemical emulsions of the present invention were not achievable in the prior art and did not exist absent the unique processing technique of the present invention. Previously, only perfluorochemical emulsions having concentrations of perfluorochemical of 10 to approximately 50% were possible, depending upon the emulsifier used and its amount.

EXAMPLE XIII

A 20 weight/volume percent emulsion of perfluorodecalin in LIPOSYN ®II emulsion was prepared for injection into rabbits to demonstrate utility and lack of toxicity. Four rabbits (approximately 3000 grams) were administered 0.125 ml/Kg Innovar-vet, an analgesic/sedative drug subcutaneously 20 minutes prior to the procedure. With regard to three of the rabbits, when the animal was stable (20+ minutes after injection) 30–50 ml of whole blood was removed through the central ear artery and infusion of an equal volume of the perfluorodecalin - LIPOSYN ® II emulsion was made. One animal was administered 20 ml of the emulsion directly without any blood removed. The total blood emulsion replacement ranged from 14–24 vol % of the animal. After 30 days, no overt toxicity was observed based upon gross behavioral or physiological symptoms.

Although this example uses only a 20 weight/volume percent emulsion, it is none-the-less indicative of the non-toxic characteristic of these types of emulsions.

The novel emulsions of the present invention have utility for enhancing the transport of oxygen through the vascular system and into the tissue of mammals which comprises administering a volumetric amount of a perfluorochemical emulsion to said mammal sufficient to maintain the total vascular volume of said mammal and subjecting the respiratory function of the mammal to elevated concentrations of oxygen above atmospheric concentrations wherein said emulsion comprises 60–90 weight/volume % or greater of a perfluorochemical. 0.5 up to 7 weight % of a phospholipid which emulsifies said perfluorochemical, 5–30 weight % of a triglyceride of fatty acids, and the remainder of an aqueous medium.

The present emulsions have a further utility of preserving internal organs outside the body which comprises perfusing the same with a preoxygenated perfluorochemical emulsion comprising 60–90 weight/volume % or greater perfluorochemical, 0.5 up to 7 weight % of a phospholipid which emulsifies said perfluorochemical, 5–30 weight % of a triglyceride of fatty acids, and the remainder of an aqueous medium.

The perfluorochemical emulsions of the present invention contain very fine particle sizes below that previously generally recorded in the prior art, which particles do not aggregate into coarse particles during normal storage of the emulsion for considerable periods of time. Accordingly, the perfluorochemical emulsions can be administered to mammals without harm to tissue due to the aggregation of particles. Furthermore, the perfluorochemical compounds used in the present invention are easily excreted through respiration when administered in the form of an emulsion as a blood substitute and no accumulation thereof in the liver or spleen has been observed. The perfluorochemical emulsion of the present invention can be administered intravenously to animals or patients suffering from bleeding or blood loss when accompanied with containment of the animal or patient under an increased oxygen content atmosphere. Besides the utility of blood substitution for mammals, the emulsions of the present invention can be used as perfusate for the preservation of internal organs, such as in procedures dictated by organ transplants and can be used in cancer therapy.

The high concentrations (60–90 wt/vol % or greater) perfluorochemical emulsions of the present invention are an important advance over the 10–50 wt/vol % prior emulsions because the high concentration emulsions when administered as a blood substitute would typically involve only a partial replacement of total blood volumes in a mammal. Accordingly, once transfused, the concentration of oxygen-carrying perfluorochemical in the total intravascular system is diluted considerably. If the high concentrations of the present invention are not used during transfusion, then upon dilution the perfluorochemical concentration does not provide adequate oxygen-carrying ability.

Additionally, when the prior low concentration (10–50 wt/vol %) perfluorochemical emulsions are used as blood substitutes, the mammal must still breathe approximately 100% humidified oxygen in order to have acceptable oxygen-uptake. Breathing 100% oxygen for an extended period of time (greater than 24 hours) has been shown to have toxic effect. However, when at least the 60 wt/vol % perfluorochemical emulsions of the present invention are used, the atmosphere breathed by the perfluorochemical transfused mammal Can be reduced to 60% oxygen, which atmosphere has been shown to be non-toxic to mammals for an extended period of time (greater than 30 days). Under conditions of high blood replacement (blood loss) or for anemic patients, it may be impossible to provide sufficient additional oxygen by oxygen-carrying capacity using the dilute emulsions of the prior art and any partial pressure of oxygen (up to and including 100% $O_2$) in the breathing atmosphere to sustain the patient. However, with the concentrated emulsions of the present invention, sufficient additional oxygen by oxygen-carrying capacity is available to sustain the patient and at decreased oxygen concentration breathing atmospheres.

The perfluorochemical emulsions of the present invention provide stability of perfluorochemical in an aqueous emulsion and particularly by using triglycerides to emulsify the preferred perfluorochemical, namely perfluorodecalin, the present invention provides high concentration emulsions which also overcome the specific problem of stable emulsification of perfluorodecalin documented in the prior art. For instance, Edward M. Levine and Alan E. Friedman describe in their paper "Artificial Blood on the Laboratory Horizon" published in LAB WORLD, October 1980 at page 56, that;

"The most extensively studied perfluorochemicals have been perfluorotributylamine and perfluorodecalin. Perfluorotributylamine forms extremely stable emulsions., however, it remains in the body for extensive periods. Perfluorodecalin leaves the body in 50 hours but is difficult to emulsify. Also, emulsions containing perfluorodecalin must be stored frozen. since they have a very limited stability at room temperature."

These prior art problems of emulsifying perfluorodecalin were further documented by Jean G. Riess in his article "Reassessment of Criteria for the Selection of Perfluorochemicals for Second-Generation Blood Substitutes: Analysis of Structure/Property Relationships", published in ARTIFICIAL ORGANS, 8(1):44–56 Raven Press, New York in 1984, wherein it is stated;

"The tenacious efforts of the late Dr. Ryoichi Naito led, in 1978, to the development by The Green Cross Corporation (Osaka, Japan) of the first and still the only commercially available standard emulsion of perfluorochemicals (F-chemicals=highly fluorinated organic materials) suitable for research and clinical testing as a blood substitute - Fluosol-DA (1,2). The advent of Fluosol-DA was therefore an essential milestone in the progress of research in this field. It permitted the first clinical tests of an F-chemical-based blood substitute, and at the end of 1982, >500 patients, mainly in Japan and in the United States, had received Fluosol-DA. For recent reviews and symposia on F-chemical-based blood substitutes, see references 3-12.

In spite of its merits, not the least of which is its very existence, which permitted numerous research groups to progress, this "first-generation" preparation should be considered as only a first draft. Among its imperfections are that it is based on two oxygen carriers. F-decalin (70%) and F-tripropylamine (30%), with widely different characteristics: the latter carrier having an overlong half-retention time in the organism $t_{\frac{1}{2}} = \sim 65$ days compared with 6 days for the former. Further, these F-chemicals contain several percent impurities. Still another problem is the limited storage stability of the emulsion, which makes it necessary to transport and store it in the frozen state. The use of a dual fluorocarbon carrier system was devised as a makeshift solution to circumvent the failure to achieve stable emulsions of F-decalin by the addition of F-tripropylamine, but at the expense of the much longer retention of the latter in the organs."

This difficulty in emulsifying and retaining stability of any appreciable amount of perfluorodecalin in a biocompatible emulsion was further alluded to by Henry Sloviter in U.S. Pat. No. 4.397,870, wherein he used large (7-9%) amounts of lecithin to emulsify perfluorodecalin in an aqueous phase and then taught that after administration of the emulsion to a patient, additional administrations of lecithin would be necessary to maintain the perfluorodecalin in emulsion in the bloodstream.

The present invention, by using triglycerides in the recited amount, has overcome the difficulties of the prior art by producing long termstable, physiologically acceptable, aqueous emulsions of perfluorochemicals and particular perfluorodecalin at very high concentrations. Although the inventors do not wish to be held to any particular theory concerning the success of these emulsions, it is believed that the triglyceride constitutes an interface between the perfluorochemical particle and the emulsifier comprising the micelle in the aqueous continuous phase of the emulsion. By existing at the interface of the perfluorochemical and the emulsifier, the triglyceride which is more polar than mono- or diglycerides provides greater stability for the non-polar characteristics of the perfluorochemical and the polar characteristics of the continuous aqueous phase. This enhanced emulsifying capability of the triglycerides is exhibited by the stable emulsions demonstrated in the present examples which provides perfluorochemical emulsions having demonstrated long term stability. When such triglycerides are used in conjunction with the novel processing or emulsification techniques of the present invention the result is a, not only stable, but high concentration emulsion, using less lecithin and having decidedly more oxygen-carrying perfluorochemical.

Although the present invention has been described in accordance with several preferred embodiments, the scope of this invention should not be limited to such specific embodiments, but rather should be ascertained from the claims which follow:

We claim:

1. A stable aqueous emulsion of a perfluorochemical comprising approximately 60 weight/volume percent or greater of a perfluorochemical, approximately 0.5 up to 7 weight % of a phospholipid which emulsifies said perfluorochemical, approximately 5–30 weight % of a triglyceride of fatty acids, and the remainder of an aqueous medium.

2. The emulsion of claim 1 wherein the perfluorochemical is selected from the group consisting of perfluoroalkylcyclohexane having 3 to 5 carbon atoms in the alkyl group, perfluorooctylbromide, perfluorodecalin and perfluoromethyldecalin.

3. The emulsion of claim 1 wherein the perfluorochemical is perfluorodecalin.

4. The emulsion of claim 1 wherein the perfluorochemical is present in the amount of approximately 75 weight/volume %.

5. The emulsion of claim 1 wherein the phospholipid is an egg phosphatide.

6. The emulsion of claim 1 wherein the phospholipid is present in a range of approximately 1–2 weight percent.

7. The emulsion of claim 1 wherein the triglyceride of fatty acids is selected from the group consisting of safflower oil, soybean oil and mixtures thereof.

8. The emulsion of claim 1 wherein the triglyceride of fatty acids is present in the range of approximately 10 to 20 weight %.

9. The emulsion of claim 1 wherein the triglyceride of fatty acids is present in approximately 20 weight %.

10. The emulsion of claim 1 including an additional emulsifier adjuvant of an acetylenic diol.

11. A stable emulsion in a physiologically acceptable aqueous medium of an oxygen-transferable saturated perfluorodecalin having essentially no detectable hydrogen or olefinic character and a mean particle size of about 0.15 microns which comprises said perfluorodecalin in a concentration of 60 to 90 weight/volume %, a phospholipid as an emulsifier in a concentration of approximately 1.2 weight %. at least one triglyceride of fatty acids as an emulsifier adjuvant in a concentration of 10 to 20 weight % wherein the fatty acids have 16 to 18 carbon atoms, and glycerin in an amount of approximately 2.5 weight %. said emulsion being suitable for use as a blood substitute.

12. The emulsion of claim 11 including an additional emulsifier adjuvant of an acetylenic diol and a polyoxyethylene, polyoxypropylene copolymer.

13. The emulsion of claim 11 including an albumin component.

14. A method of enhancing the oxygen carrying capacity of oxygen through the vascular system and into the tissue of mammals which comprises administering a volumetric amount of a perfluorochemical emulsion to said mammal sufficient to maintain the total vascular volume of said mammal and subjecting the respiratory function of the mammal to elevated concentrations of oxygen above atmospheric concentrations wherein said emulsion comprises approximately 60 weight/volume % or greater of a perfluorochemical, approximately 0.5 up to 7 weight % of a phospholipid which emulsifies said perfluorochemical, approximately 5-30 weight % of a triglyceride of fatty acids, and the remainder of an aqueous medium.

15. A method of preserving internal organs outside the body which comprises perfusing the same with a preoxygenated perfluorochemical emulsion comprising approximately 60 weight/volume % or greater of a perfluorochemical, approximately 0.5 up to 7 weight % of a phospholipid which emulsifies said perfluorochemical, approximately 5-30 weight % of a triglyceride of fatty acids, and the remainder of an aqueous medium.

16. The method for preparing a stable aqueous emulsion of a perfluorochemical in a perfluorochemical concentration range of approximately 60 wt/vol % or greater wherein an aqueous emulsifier is mixed with a first portion of the perfluorochemical volume maintaining a temperature below 35° C. to produce an initial perfluorochemical emulsion and thereafter mixing the remaining portion of the perfluorochemical volume to the initial perfluorochemical emulsion while maintaining a temperature below 35° C. to result in a final aqueous perfluorochemical emulsion having a perfluorochemical concentration in the range of 60 wt/vol % or greater.

17. The method of claim 16 wherein the emulsion during mixing is maintained at a temperature no greater than 20° C.

18. The method of claim 16 wherein the mixing is a high shear mixing.

19. The method of claim 16 wherein the first portion of perfluorochemical mixed with the emulsifier is approximately half of the total perfluorochemical volume to be emulsified.

20. The method of claim 16 wherein the perfluorochemical is prepared by initial fluorination of a chemical in the presence of cobalt trifluoride and subsequent complete fluorination of said chemical in the presence of elemental fluorine.

* * * * *